(12) United States Patent
Lustig et al.

(10) Patent No.: US 8,394,962 B2
(45) Date of Patent: Mar. 12, 2013

(54) METHOD FOR THE PREPARATION OF DABIGATRAN AND ITS INTERMEDIATES

(75) Inventors: Petr Lustig, Pardubice (CZ); Josef Jirman, Prague (CZ)

(73) Assignee: Zentiva k.s., Prague (CZ)

( * ) Notice: Subject to any disclaimer, the term of this patent is extended or adjusted under 35 U.S.C. 154(b) by 41 days.

(21) Appl. No.: 13/124,034

(22) PCT Filed: Oct. 26, 2009

(86) PCT No.: PCT/CZ2009/000127
§ 371 (c)(1),
(2), (4) Date: May 26, 2011

(87) PCT Pub. No.: WO2010/045900
PCT Pub. Date: Apr. 29, 2010

(65) Prior Publication Data
US 2011/0224441 A1    Sep. 15, 2011

(30) Foreign Application Priority Data
Oct. 24, 2008    (CS) .................... 2008-669

(51) Int. Cl.
*C07D 401/12* (2006.01)
(52) U.S. Cl. .................. 546/273.4
(58) Field of Classification Search ........... 546/273.4
See application file for complete search history.

(56) References Cited

U.S. PATENT DOCUMENTS
| 6,087,380 A | 7/2000 | Hauel et al. |
| 6,469,039 B1 | 10/2002 | Hauel et al. |
| 2006/0004064 A1 | 1/2006 | Zerban et al. |

FOREIGN PATENT DOCUMENTS
| WO | WO 2007/712742 | 6/2007 |
| WO | WO 2009/111997 | 9/2009 |

OTHER PUBLICATIONS

International Search Report of Applicatin No. PCT/CZ2009/000127 mailed on Feb. 3, 2010.

*Primary Examiner* — Patricia L Morris
(74) *Attorney, Agent, or Firm* — Pearl Cohen Zedek Latzer, LLP

(57) ABSTRACT

Intermediates for the preparation of dabigatran of formulae (VII-2HCl) and (VII-HCl), methods for their preparation and a method for preparation of dabigatran of formula (VIII) using these intermediates.

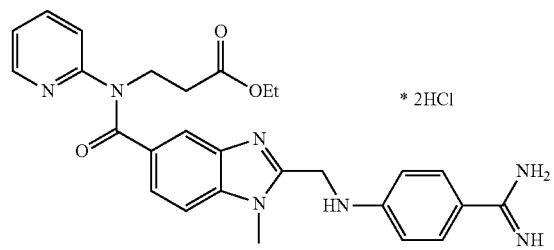

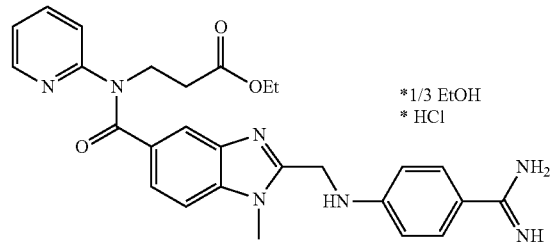

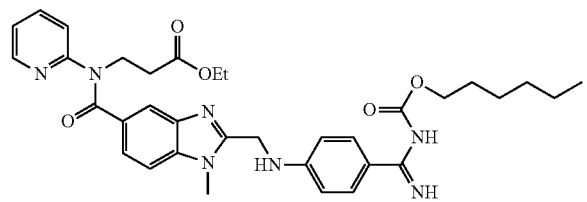

2 Claims, No Drawings

METHOD FOR THE PREPARATION OF DABIGATRAN AND ITS INTERMEDIATES

CROSS-REFERENCE TO RELATED APPLICATIONS

This application is a National Phase Application of PCT International Application No. PCT/CZ2009/000127, International Filing Date Oct. 26, 2009, claiming priority of Czech Republic Patent Application, PV2008-669, filed Oct. 24, 2008.

TECHNICAL FIELD

The invention deals with a new method for the manufacture of 3-([2-[[(4-(N-n-hexyloxycarbonylcarbamimidoyl)-phenylamino]-methyl]]-1-methyl-1H-benzimidazole-5-carbonyl]-pyridin-2-yl-amino)ethyl propionate of formula VIII

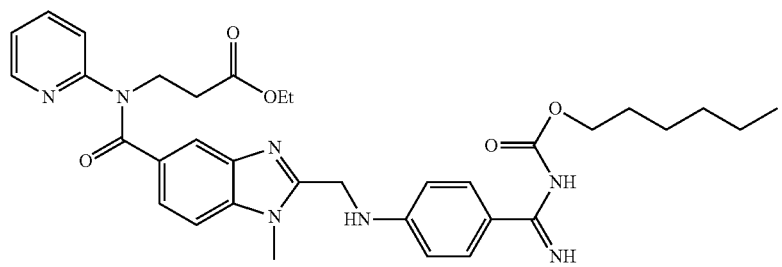

known under the non-proprietary name dabigatran. Dabigatran is an anticoagulant agent and is used for treatment of thromboses, cardiovascular diseases, and the like.

BACKGROUND ART

Preparation of dabigatran was first described in the document no. WO 9837075; however, this method brings many technological problems, e.g. very complicated purifying operations, problems with low purity of intermediate products and the resulting low yield and low purity of the final product.

One of the advanced intermediates during the production of dabigatran is the substance of formula VI.

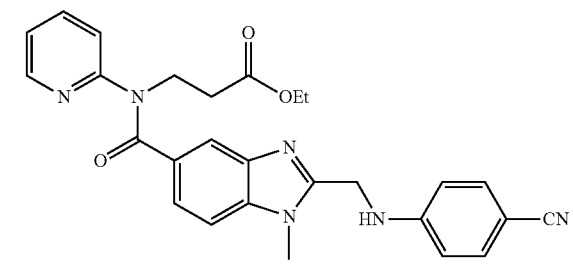

The com=pound of formula VI is prepared by a reaction of substance IV with reagent V as shown in Scheme 1.

Scheme 1

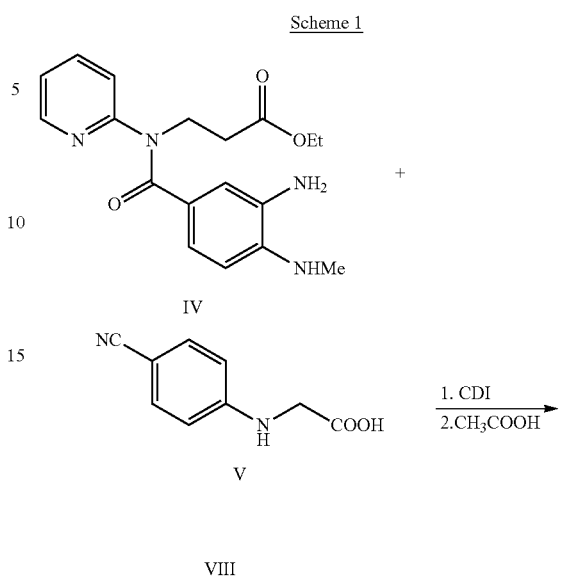

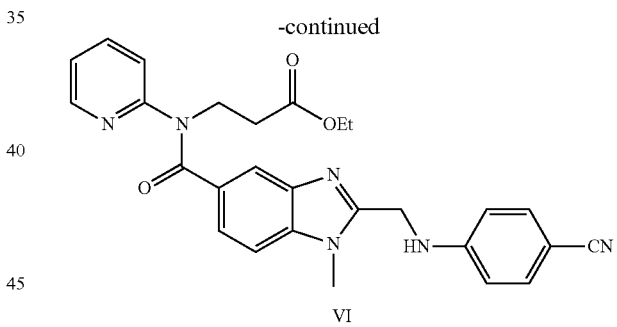

The procedure described in WO 9837075 produces compound VI in the form of its base or acetate. Both these products require chromatographic purification, which is very difficult to apply in the industrial scale. This purification method burdens the process economy very much and has a negative impact on the yield.

In the next stage acidic hydrolysis of the nitrile function of compound VI and a reaction with ammonium carbonate is performed to produce the substance of formula VII. The reaction is shown in Scheme 2.

Scheme 2

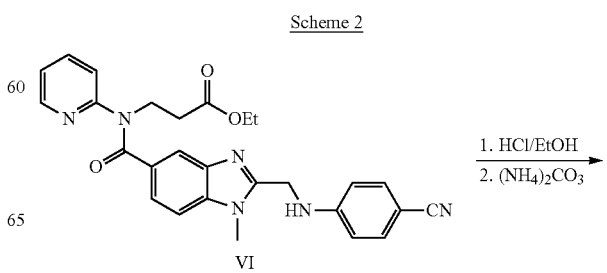

VII

The procedure in accordance with WO 9837075 produces substance VII in the monohydrochloride form.

When reproducing the procedure of WO 9837075 we found out, in line with WO 9837075, that compound VII prepared by this method required subsequent chromatographic purification as it was an oily substance with a relatively high content of impurities. We did not manage to find a solvent that would enable purification of this substance by crystallization.

The last stage is a reaction of intermediate VII with hexyl chloroformate producing dabigatran and its transformation to a pharmaceutically acceptable salt; in the case of the above mentioned patent application it is the methanesulfonate.

However, the method in accordance with WO 9837075 does not make it possible to prepare dabigatran with high purity, which is required in the case of a pharmaceutical substance, and in a yield acceptable in the industrial scale.

The reason is mainly low purity of the intermediate products, which are moreover produced in forms requiring complicated purification with the use of chromatographic methods.

DISCLOSURE OF INVENTION

The present invention provides preparation and use of new, not yet described advanced intermediates of dabigatran:
the monohydrochloride of compound VII in the form of a solvate with ethanol of formula VII-HCl VII-HCl and the dihydrochloride of compound VII of formula VII-2HCl VII-2HCl and a new method of preparation of dabigatran based on these intermediates.

Isolation of either of the two intermediates will considerably increase the purifying ability of crystallization in comparison to crystallization of the hitherto described hydrochloride.

The procedure in accordance with WO 9837075 provides product VII in the quality of 85-90%. Transformation of this compound to VII-HCl and its crystallization improves its quality to 93-95%. Preparation of compound VII-2HCl leads to further quality improvement, namely to 96-98%.

Preparation of the above mentioned salts allows avoiding chromatographic purification of substance VII, which is described in patent no. WO 9837075, and is necessary for obtaining compound VII with high quality.

The preparation of the compound of formula VII

VII is carried out by acidic hydrolysis of the nitrile function of compound VI with subsequent reaction with ammonium carbonate (see Scheme 2).

Use of the starting substance VI in the oxalate form in accordance with the presented procedure produces the monohydrochloride of compound VII in the form of a solvate with ethanol of formula VII-HCl.

VII-HCl

This approach has a considerable purifying effect, which leads to the production of the intermediate of formula VII-HCl with high purity (88-90%) and a higher yield (85-90%). Substance VII-HCl can be re-purified by crystallization as contrasted to VII prepared in accordance with WO 9837075, which can only be purified with the use of chromatographic methods. This way the purity of compound VII-HCl can be increased to the content of 90-95%.

An even higher purifying effect was achieved by preparation of the dihydrochloride of compound VII of formula VII-2HCl.

VII-2HCl

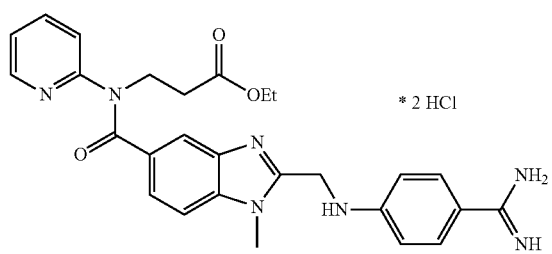

A solution of dry hydrogen chloride in a solvent selected e.g. from the group of ethers, esters, ketones or alcohols is added dropwise to a solution of substance VII-HCl under stirring.

Alcohols appear to represent the most suitable solvents. This compound can also be purified by crystallization. This way, a product with a very high purity (96-98%) is obtained.

The preparation of compound VII in the form of the above mentioned salts enables their purification by crystallization as contrasted to compound VII obtained in accordance with the method of document WO 9837075, where it is necessary to purify compound VII with the use of chromatographic methods. Consequently, this means very significant simplification and improvement of efficiency of the whole production process since chromatographic purification represents a serious technological as well as economical problem in industrial applications.

In addition, the method in accordance with the present invention produces the intermediates of dabigatran, i.e. VII-HCl and VII-2HCl, with very high purity necessary for the preparation of a high-quality pharmaceutical substance.

The last stage is a reaction of the intermediate VII-HCl or VII-2HCl with hexyl chloroformate producing dabigatran and its transformation to a pharmaceutically acceptable salt.

The reaction is carried out in an inert solvent selected from aromatic hydrocarbons, ethers, chlorinated hydrocarbons, nitriles and ketones in the presence of a suitable base, either organic or inorganic (tertiary amines, cyclic tertiary amines, hydroxides, carbonates).

A preferable embodiment of the entire procedure in accordance with the presented invention is shown in Scheme 3.

The invention also includes a convenient process of obtaining new intermediates. The purifying abilities of the described solvate or dihydrochloride can be advantageously combined with those of the salts of their precursors. This method enables preparation of dabigatran with high purity and in an industrially acceptable yield. The change of purification operations allowed by the use of these salts, i.e. replacement of chromatographic purification with crystallization, leads to a considerable improvement of economy of the whole production process.

The salt of oxalic acid of formula VI-oxal has proved to be especially convenient for these purposes.

VI-oxal

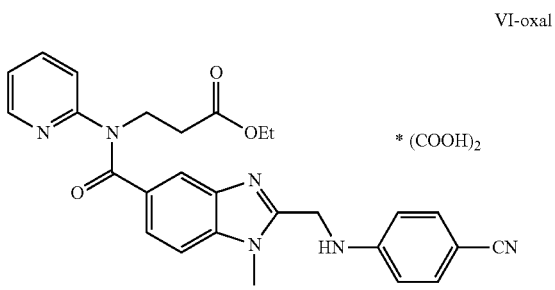 [SMILES: CCOC(=O)CCN(C(=O)c1ccc2c(c1)nc(CNc1ccc(C#N)cc1)n2C)c1ccccn1]

This starting compound can be prepared by the procedure illustrated in Scheme 4.

Compound IV reacts with substance V with the use of oxalic acid.

Scheme 4

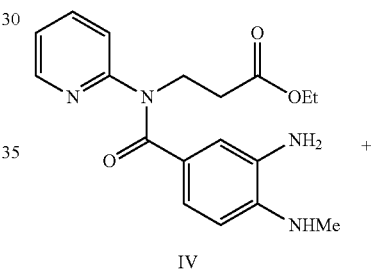

IV

Scheme 3

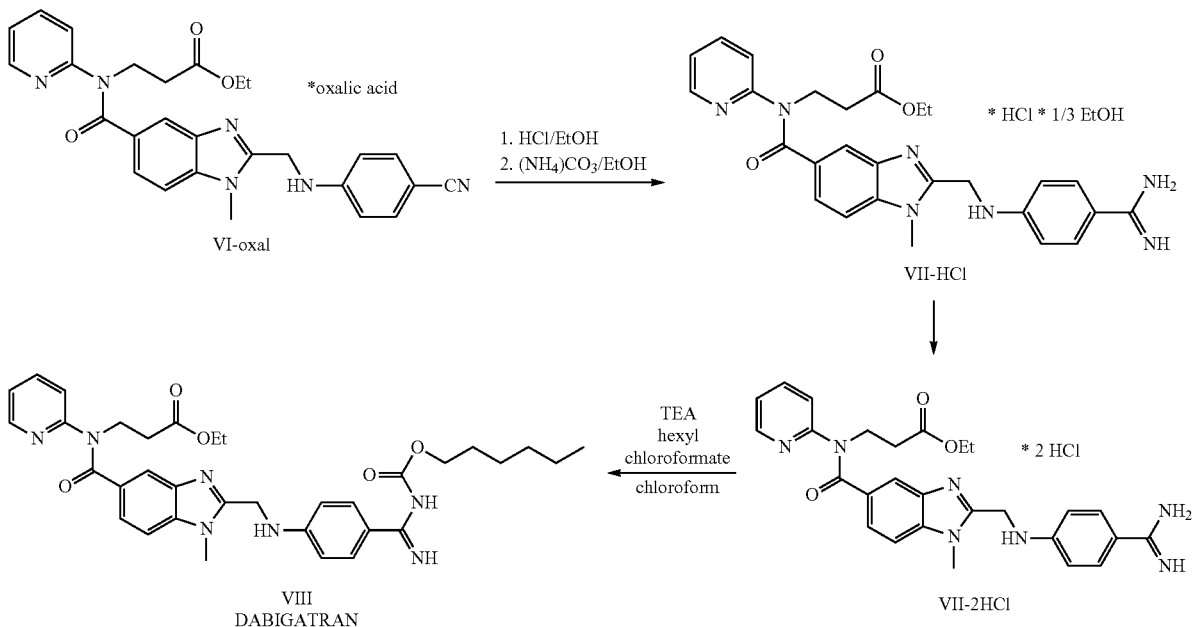

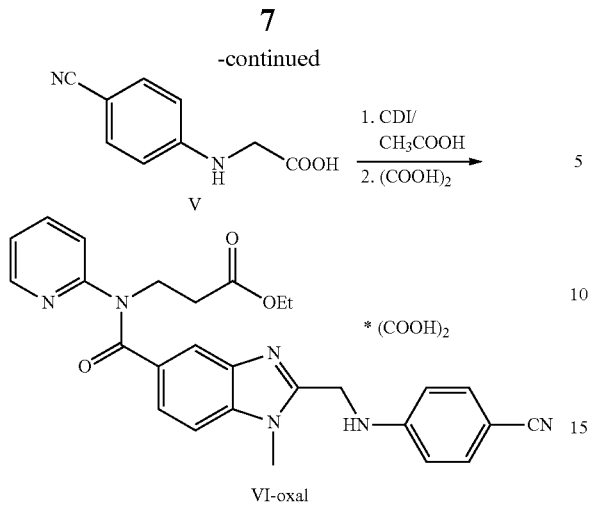
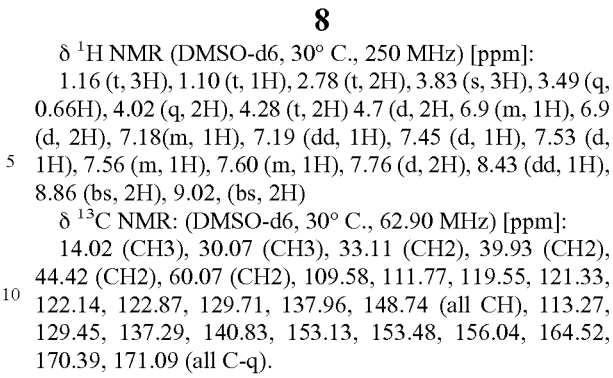

Compound VI prepared by the method in accordance with WO 9837075 is in the acetate form. Both these products require chromatographic purification, which is very difficult to realize in the industrial scale.

In the procedure in accordance with the presented invention compound VI is obtained in the form of a salt with oxalic acid. This salt is simply re-purified by further crystallization and this way the advanced intermediate VI is obtained with high purity and in the yield that is acceptable for industrial production, of approximately 60 to 80%.

This crystallization can be performed from a polar protic organic solvent, preferably from lower $C_1$ to $C_5$ alcohols, e.g. from ethyl alcohol.

The procedure in accordance with the presented invention enables production of a high-quality product with a low content of impurities (product content: 98%) and with a high yield (65-70%).

The production of intermediates VI and VII in the form of the following salts: VI-oxal, VII-HCl and VII-2HCl will significantly simplify purification operations during the production of dabigatran. The chromatographic purification mentioned in WO 9837075 cannot be used in the industrial scale. Replacement of chromatographic purification with crystallization represents a considerable technological simplification and improves the economy of the entire production process.

The invention is further demonstrated in the following examples:

EXAMPLE 1

Preparation of VII-HCl 40 g of compound VI-oxal are put into ethanol containing hydrogen chloride. This mixture is stirred at the laboratory temperature for 14 hours. Then, ethanol with hydrogen chloride is evaporated and the evaporation residue is dissolved in 1000 ml of ethanol. 110 g of ammonium carbonate are added to this solution and the whole mixture is stirred at the laboratory temperature for 26 hours. After expiration of this time period the undissolved fraction is removed by aspiration and the filtrate is concentrated. The resulting product is dissolved in 560 ml of a 2:1 mixture of ethyl acetate and ethanol at the laboratory temperature. After 30 minutes a white precipitate results, which is cooled in a refrigerator and aspirated and dried at 50° C.

Yield: 28.5 g (81%); content according to HPLC: 89%. According to NMR the product is a solvate with ethanol in the proportion of 3:1 (VII-HCl).

δ $^1$H NMR (DMSO-d6, 30° C., 250 MHz) [ppm]:
1.16 (t, 3H), 1.10 (t, 1H), 2.78 (t, 2H), 3.83 (s, 3H), 3.49 (q, 0.66H), 4.02 (q, 2H), 4.28 (t, 2H) 4.7 (d, 2H, 6.9 (m, 1H), 6.9 (d, 2H), 7.18(m, 1H), 7.19 (dd, 1H), 7.45 (d, 1H), 7.53 (d, 1H), 7.56 (m, 1H), 7.60 (m, 1H), 7.76 (d, 2H), 8.43 (dd, 1H), 8.86 (bs, 2H), 9.02, (bs, 2H)

δ $^{13}$C NMR: (DMSO-d6, 30° C., 62.90 MHz) [ppm]:
14.02 (CH3), 30.07 (CH3), 33.11 (CH2), 39.93 (CH2), 44.42 (CH2), 60.07 (CH2), 109.58, 111.77, 119.55, 121.33, 122.14, 122.87, 129.71, 137.96, 148.74 (all CH), 113.27, 129.45, 137.29, 140.83, 153.13, 153.48, 156.04, 164.52, 170.39, 171.09 (all C-q).

EXAMPLE 2

Preparation of VII-2HCl 9.7 g of compound VII-HCl-EtOH are dissolved in a mixture of ethanol with ethyl acetate. A solution of hydrogen chloride in ethanol containing an equimolar amount of the acid is added to this solution dropwise. After separation of the precipitate the suspension is cooled and the product is aspirated and dried.

Yield: 9.1 g (87.8%); content according to HPLC: 96.2%.

δ $^1$H NMR: δ $^1$H NMR (DMSO-d6, 30° C., 250 MHz) [ppm]:
1.16 (t, 3H), 2.56 (t, 2H), 4.03 (m, 5H), 4.26 (t, 2H), 5.04 (bs. 2H), 6.99 (d, 2H), 7.13(d, 1H), 7.21 (dd, 1H), 7.41 (dd, 1H), 7.68 (m, 1H) 7.71 (d, 1H), 7.82 (d, 2H), 7.84 (d, 1H), 8.41 (dd, 1H), 8.99 (bs, 2H), 9.17, (bs, 2H)

δ $^{13}$C NMR: (DMSO-d6, 30° C., 62.90 MHz) [ppm]:
14.03 (CH3), 31.51 (CH3), 32.91 (CH2), 39.59 (CH2), 44.56 (CH2), 60.11 (CH2), 112.12, 112.25, 115.20, 121.94, 122.12, 125.35, 129.80, 138.48, 148.87 (all CH), 114.59, 130.73, 133.43, 134.24, 152.42, 153.69, 155.33, 164.50, 168.96, 171.00 (all C-q).

EXAMPLE 3

Preparation of Dabigatran Mesylate

To 9.1 g of compound VII-2HCl (0.016 mol) 270 ml of chloroform and 9 ml (0.064 mol) of triethylamine are added. Then, a solution of 3.1 ml (0.018 mol) of hexyl chloroformate in chloroform is added dropwise at the laboratory temperature. After one hour the reaction mixture is shaken with brine and the organic layer is separated, which is dried with sodium sulfate and concentrated. The obtained evaporation residue is crystallized from ethyl acetate.

Yield: 8.6 g (86%)

This product is dissolved in acetone and an equimolar amount of methanesulfonic acid is added dropwise. The separated precipitate is aspirated and dried at the laboratory temperature.

Yield: 75%; content according to HPLC: 99.5%.

EXAMPLE 4

Preparation of Dabigatran Mesylate 9 g of compound VII-HCl (0.017 mol) were dissolved in 300 ml of chloroform. 6 ml of triethylamine were added to this solution and then a solution of 3.4 ml (0.02 mol) of hexyl chloroformate in chloroform was added dropwise. After one hour the reaction mixture is shaken with brine, the organic layer is separated, which is dried with sodium sulfate and concentrated. The obtained evaporation residue is crystallized from ethyl acetate.

Yield: 9.6 g (90%)

This product is dissolved in acetone and an equimolar amount of methanesulfonic acid is added dropwise. The separated evaporation residue is aspirated and dried at the laboratory temperature.

Yield: 73%; content according to HPLC: 99.5%.

The invention claimed is:

1. A method for the manufacture of dabigatran, wherein the compound of formula VII-2HCl

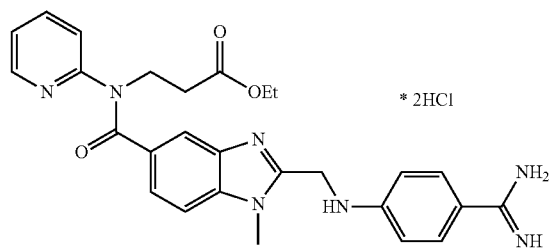

VII-2HCl

*2HCl or of formula VII-HCl

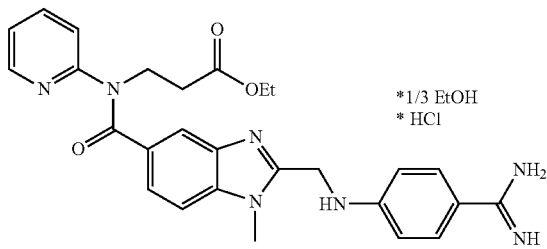

VII-HCl

*1/3 EtOH
* HCl is reacted with hexyl chloroformate in the presence of an inorganic or organic base in an inert solvent selected from ethers, ketones, chlorinated hydrocarbons or acetonitrile and the obtained dabigatran is transformed to a pharmaceutically acceptable salt.

2. The method according to claim 1, wherein the reaction is carried out in a chlorinated hydrocarbon in the presence of a tertiary amine as the base.

* * * * *